United States Patent [19]

Känel et al.

[11] Patent Number: 5,527,917

[45] Date of Patent: Jun. 18, 1996

[54] PROCESS FOR THE PREPARATION OF 1,2-BENZISOTHIAZOLES

[75] Inventors: Hans-Ruedi Känel, Bubendorf; Arthur Wegmann, Kaisten; Denis Neff, Monthey, all of Switzerland

[73] Assignee: Ciba-Geigy Corporation, Tarrytown, N.Y.

[21] Appl. No.: 301,467

[22] Filed: Sep. 7, 1994

[30] Foreign Application Priority Data

Sep. 13, 1993 [CH] Switzerland .......................... 2736/93
Jul. 6, 1994 [CH] Switzerland .......................... 2159/94

[51] Int. Cl.⁶ ................................................ C07D 275/04
[52] U.S. Cl. .......................................................... 548/207
[58] Field of Search .............................. 564/259; 548/207

[56] References Cited

U.S. PATENT DOCUMENTS

| | | | |
|---|---|---|---|
| 4,939,302 | 7/1990 | Roberts | 568/55 |
| 5,169,951 | 12/1992 | Sutter et al. | 548/212 |
| 5,260,485 | 11/1993 | Calbick et al. | 568/8 |

FOREIGN PATENT DOCUMENTS

| | | |
|---|---|---|
| 0039795 | 11/1981 | European Pat. Off. |
| 0454621 | 10/1991 | European Pat. Off. |
| 0530136 | 3/1993 | European Pat. Off. |

OTHER PUBLICATIONS

J. Chem. Soc., Perkin Trans. I, 1973 pp. 356–359, K. Clarke et al.
Adv. Heterocycl Chem., 38, 1985, pp. 106–133, M. Davis.
Can. J. Chem., 66, No. 6, 1988, pp. 1405–1409, D. M. McKinnon et al.
Chem. Abstract, vol. 59, 872(d) (1963).
Ann. Chim. (Roma), vol. 53, pp. 577–587, (1963).
Ann. Chim. (Roma), vol. 53/12, pp. 1860–1868 (1963).
Chemical Abstracts, vol. 60, 12000(d) (1964).
J. Chem. Soc. (C) 1971, pp. 3994–3999.
J. Org. Chem., vol. 43, No. 9, 1978, pp. 1824–1825.
Phosphorus and Sulfur, 1982, vol. 12, pp. 357–367.
Liebigs Ann. Chem. (1980), pp. 768–778.
L. K. A. Rahman et al., J. Chem. Soc. Perkin Trans. I, pp. 385–390 (1984).
O. Meth–Cohn et al., Synthesis, 1, pp. 58–60 (1978).
D. M. McKinnon et al., J. Heterocyclic Chem., 28, pp. 445–448 (1991).
D. M. McKinnon et al., Can. J. Chem., 66, 1405–1409 (1988).

*Primary Examiner*—Johann Richter
*Assistant Examiner*—Laura R. Cross
*Attorney, Agent, or Firm*—Edward McC. Roberts

[57] ABSTRACT

A process for the preparation of 1,2-benzisothiazoles of formula I

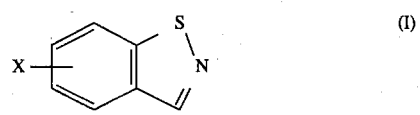

wherein

X is in any one of the 4 possible positions of the benzene ring and is hydrogen, halogen, nitro, $C_1$–$C_4$alkoxy, halo-$C_1$–$C_4$alkoxy, $C_2$–$C_4$alkenyloxy or $C_2$–$C_4$alkynyloxy, in which process a compound of formula II

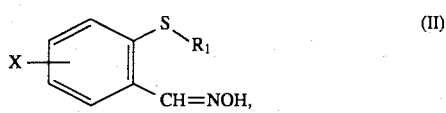

wherein X is as defined for formula I and $R_1$ is hydrogen or an unsubstituted or substituted $C_1$–$C_{12}$hydrocarbon radical, is reacted in the presence of a catalytic amount of a strong acid.

Compounds of formula I are known as pesticides, especially as nematicides.

13 Claims, No Drawings

PROCESS FOR THE PREPARATION OF 1,2-BENZISOTHIAZOLES

The invention relates to a process for the preparation of 1,2-benzisothiazoles of formula I

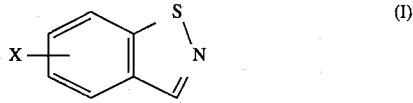 (I)

wherein X is in any one of the 4 possible positions of the benzene ring and is hydrogen, halogen, nitro, $C_1$–$C_4$alkoxy, halo-$C_1$–$C_4$alkoxy, $C_2$–$C_4$alkenyloxy or $C_2$–$C_4$alkynyloxy, in which process a compound of formula II

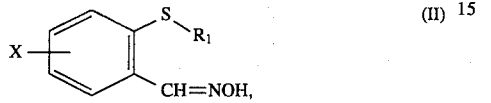 (II)

wherein X is as defined for formula I and $R_1$ is hydrogen or an unsubstituted or substituted $C_1$–$C_2$hydrocarbon radical, is reacted in the presence of a catalytic amount of a strong acid.

Compounds of formula I are known as pesticides, especially as nematicides (see, for example, EP-A-454 621 and EP-A-530 136).

It is known that benzisothiazoles can be prepared from 2-(alkylthio)benzaldehydes by reaction with hydroxylamine-O-sulfonic acid and subsequent ring-closure in solution (see, for example, EP-A-454 621). In that synthesis, a reactant is temporarily introduced into the molecule and is largely removed again during the ring-closure reaction; the resulting disadvantages as regards industrial synthesis are an undesirable amount of material to be handled, an insufficient yield in terms of volume and a high degree of waste water contamination. A further disadvantage of that process resides in the fact that the reaction mixture is thermally unstable in the region of the reaction temperature and may therefore constitute a safety risk.

It is also known that benzisothiazoles can be prepared by the ring-closure of 2-mercaptobenzaldehyde oximes (see, for example, Ann. Chim. (Rome) Vol. 53, 1963, pages 577 . 587) or by the ring-closure of 2-(alkylthio)benzaldehyde oximes (see, for example, Synthesis 1978, pages 58–60; EP-A-530 136). In those processes, a strong acid, such as polyphosphoric acid, or phosphorus pentoxide in methanesulfonic acid, is used as the solvent. Owing to their high boiling point, those solvents, or acids, which are used in large excess, cannot be separated from the product by distillation but have to be removed from the product by washing out with water and thus contaminate the waste water to an extraordinarily high degree. A further disadvantage is that the yields are sometimes poor.

The known processes for the preparation of benzisothiazoles of formula I are accordingly unsatisfactory for economic, ecological and safety reasons.

Surprisingly, it has now been found that benzisothiazoles of formula I are obtained in very high yields and with a satisfactory degree of purity when a compound of formula II is reacted in a solvent with catalytic amounts of a strong acid.

The process according to the invention has the following advantages over the previously known processes:

yields higher than 90%, for example up to 97%;
lesser degree of secondary product formation and therefore working-up easier;
improved yields in terms of volume;
trouble-free recovery of the solvent;
less waste water contamination (ecology);
no risk of thermal decomposition of the reaction mixture;
less corrosion of the reactor.

The general terms used hereinbefore and hereinafter have the following meanings:

Halogen is, for example, fluorine, chlorine, bromine or iodine, preferably fluorine, chlorine or bromine.

Alkoxy, alkenyloxy and alkynyloxy may be straight-chained or branched, depending on the number of carbon atoms.

Alkoxy is, for example, methoxy, ethoxy, propoxy, isopropoxy, n-butoxy, isobutoxy, sec-butoxy and tert-butoxy; preferably methoxy and ethoxy.

Haloalkoxy may contain identical or different halogen atoms, for example difluoromethoxy, trifluoromethoxy, chlorofluoromethoxy, 2,2,2-trifluoroethoxy, 1,1,2,2-tetrafluoroethoxy, 2-fluoroethoxy, 2-chloroethoxy and 2,2-difluoroethoxy; preferably difluoromethoxy.

Alkenyloxy is, for example, allyloxy, methallyloxy or but-2-en-1-yloxy. Allyloxy is preferred.

Alkynyloxy is, for example, propargyloxy, but-1-yn-1-yloxy or but-2-yn-3-yloxy; propargyloxy is preferred.

Hydrocarbon radicals $R_1$ may be saturated or unsaturated, branched or unbranched, open-chained or cyclic, aromatic or araliphatic. $C_1$–$C_6$alkyl, $C_3$–$C_6$cycloalkyl, phenyl and benzyl are preferred.

Examples of open-chained saturated hydrocarbon radicals are methyl, ethyl, n-propyl, isopropyl, n-butyl, sec-butyl, isobutyl, tert-butyl, sec-amyl, tert-amyl, 1-hexyl and 3-hexyl.

Examples of open-chained unsaturated hydrocarbon radicals are allyl, methallyl, 1-methylvinyl and but-2-en-1-yl, propargyl, but-1-yn-1-yl and but-1-yn-3-yl.

Cyclic hydrocarbon radicals may be aromatic, such as, for example, phenyl and naphthyl, or non-aromatic, such as, for example, cyclopentenyl, cyclohexenyl, cycloheptenyl and cycloocmdienyl, or partially aromatic, such as, for example, tetrahydronaphthyl and indanyl, or cycloaliphatic, such as cyclopropyl, cyclobutyl, cyclopentyl, cyclohexyl and cycloheptyl, or araliphatic, such as, for example, benzyl.

$R_1$ may be substituted as desired, provided the substituent does not have an adverse effect on the reaction under the reaction conditions indicated. Examples of suitable substituents at $R_1$ are phenyl, halogen and alkoxy.

The reaction can be carried out with or without a solvent.

Solvents are, for example, aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichloromethane, dichloroethane or trichloroethane; ethers, such as diethyl ether, tert-butyl methyl ether, tetrahydrofuran or dioxane; ketones, such as acetone or methyl ethyl ketone; alcohols, such as methanol, ethanol, propanol, butanol, ethylene glycol or glycerol; esters, such as ethyl acetate or butyl acetate; amides, such as N,N-dimethylformamide, N,N-dimethylacetamide, N-methylpyrrolidone or hexamethylphosphoric acid triamide; nitriles, such as acetonitrile; sulfones, such as sulfolane; and ureas, such as dimethylpropyleneurea, and also water.

When non-polar solvents are used, such as, for example, benzene, toluene, xylene, chlorobenzene, bromobenzene, petroleum ether, hexane, cyclohexane, it may be advantageous to add a suitable phase transfer catalyst. There may be mentioned as examples: tetrabutylammonium bromide, dibenzyldimethylammonium methyl sulfate or tris[2-(2-methoxycthoxy)ethyl]amine.

In a preferred form of the process for the preparation of a compound of formula I, a polar solvent, especially water or a $C_1$–$C_6$ alcohol or a mixture thereof, is used. 1-propanol and 2-butanol are especially preferred.

Strong acids are, for example, mineral acids, such as hydrohalic acids (hydrofluoric acid, hydrochloric acid, hydrobromic acid or hydriodic acid), sulfuric acid, phosphoric acid, polyphosphoric acid, nitric acid; organic acids, such as formic acid, acetic acid, trifluoroacetic acid, trichloroacetic acid; sulfonic acids, such as benzenesulfonic acid, p-toluenesulfonic acid, methanesulfonic acid, hydroxylamine-O-sulfonic acid; and sulfinic acids, such as p-toluenesulfinic acid.

Preference is given to the preparation of compounds of formula I wherein X is halogen or nitro, especially preferably compounds wherein X is in the 7-position, 7-chlorobenzisothiazole being very especially preferred.

Preferred compounds of formula II for carrying out the process according to the invention are those wherein $R_1$ is an unsubstituted or substituted $C_1$–$C_2$ hydrocarbon radical, preferably $C_1$–$C_6$ alkyl or benzyl, very especially those wherein $R_1$ is tert-butyl.

The catalyst used is preferably a mineral acid or a sulfonic acid, especially preferably p-toluenesulfonic acid, methanesulfonic acid, hydroxylamine-O-sulfonic acid or sulfuric acid. The acid may also be bound to a solid carrier, for example to an ion exchange resin, such as Amberlyst.

The amount of catalyst is 1–50 mol %, preferably 2–15 mol %, based on the compound of formula II.

The reaction temperature may be varied from 30° C. up to the reflux temperature of the solvent; the reaction is advantageously carried out at the reflux temperature of the solvent, and solvent is distilled off continuously during the reaction.

In practice, the procedure may be, for example, as follows: all the educts are assembled, the reaction mixture is heated to boiling point and maintained under reflux for from 4 to 8 hours and then the solvent is distilled off, if desired in vacuo, and water is subsequently added to the residue. The product crystallises out and is isolated by filtration.

In a preferred form of the process, the solvent is distilled off continuously during the reaction, if desired under a slight vacuum. It is thereby possible to reduce the reaction time.

The process according to the invention can be carried out both batchwise and continuously. If the reaction is carried out continuously, it is advantageous to convey the reaction mixture, with or without the solvent, over a solid carrier to which the acid acting as the catalyst is bound.

The starting materials of formula II can be prepared by known methods in accordance with the following reaction scheme (see, for example, EP-A-454 621 and EP-A-530 136):

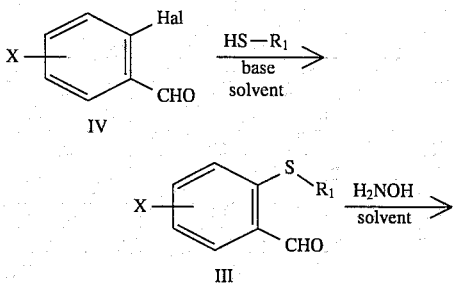

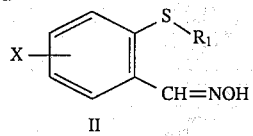

In the above formulae, $R_1$ and X are as defined above; Hal is halogen.

Preferred is the process for compounds wherein X is in the 3-position with respect to the carbaldehyde or carbaldoxime group, X and Hal are chlorine and $R_1$ is tert-butyl.

Preferred bases for the preparation of compounds of formula III are alcoholates, carbonates or hydrogen carbonates of alkali metals, especially sodium carbonate and potassium carbonate; preferred solvents are alcohols or aprotic polar solvents, with dimethylformamide, dimethylacetamide, dimethyl sulfoxide, N-methylpyrrolidone and tetrahydrofuran being especially preferred.

Compounds of formula II can be prepared by reacting a compound of formula III with hydroxylamine in a polar solvent, such as water or a $C_1$–$C_6$ alcohol or a mixture thereof; water, methanol, 1-propanol and 2-butanol and a mixture thereof are especially preferred; 1-propanol and 2-butanol are more especially preferred. Hydroxylamine is advantageously used in the form of an aqueous solution, either in free form or in the form of a salt, such as, for example, in the form of a hydrochloride, sulfate or phosphate.

It is especially advantageous to use the same solvent for that reaction as for the following stage and thus to avoid isolation of the intermediate.

A) Preparation Examples for 7-chlorobenzisothiazole (Compound IA)

EXAMPLE 1

243.7 g (1 mol) of 3-chloro-2-(tert-butylthio)benzaldehyde oxime and 9.5 g (0.05 mol) of p-toluenesulfonic acid monohydrate are maintained under reflux (95°–100° C.) for 2–4 hours in 700 ml. of 1-propanol; solvent is distilled off continuously during that period. Water is then added to the reaction mixture which remains, and the product which has crystallised out is isolated by filtration and dried; yield 165 g (97% of the theoretical yield); content >95%, m.p. 49° C.

EXAMPLE 1A

Comparison Example for the preparation of 7-chlorobenzisothiazole according to the prior art 243.7 g (1 mol) of 3-chloro-2-(tert-butylthio)benzaldehyde oxime are maintained at 65°–70° C. for 1.5 hours in 700 ml of polyphosphoric acid; after that period, according to thin-layer chromatography all of the starting material has reacted. Water is then added at 20°–30° C. and the product which has crystallised out is isolated by filtration and dried. Yield 75 g (44% of the theoretical yield).

EXAMPLE 2

243., g (1 mol) of 3-chloro-2-(n-butylthio)benzaldehyde oxime and 19 g (0.1 mol) of p-toluenesulfonic acid monohydrate are maintained under reflux (95°–100° C.) for 2–4 hours in 700 ml of 1-propanel; solvent is distilled off continuously during that period. Water and toluene are then added to the reaction mixture which remains, the toluene phase is separated off and the toluene is distilled off. Yield 197 g (66% of the theoretical yield); content 57%.

EXAMPLE 3

The procedure is as in Example 2 except that 3-chloro-2-(isopropylthio)benzaldehyde oxime is used instead of 3-chloro-2-(n-butylthio)benzaldehyde oxime. Yield 171 g (64% of the theoretical yield); content 64%.

EXAMPLE 4

243.7 g (1 mol) of 3-chloro-2-(tert-butylthio)benzaldehyde oxime are metered in the form of a melt at 110°–115° C. onto 200 g of "Amberlyst 15" (strongly acidic cation exchanger), during which operation isobutylene evolves. When metering is complete, the catalyst is filtered off from the hot melt; the oily filtrate cystallises out on cooling to room temperature. Yield 161 g (77% of the theoretical yield); content 82%.

B) Preparation Example for starting materials

EXAMPLE 5

Preparation of 3-chloro-2-(tert-butylthio)benzaldehyde oxime (Compound IIA) 35 g (1.05 mol) of hydroxylamine in the form of a 50% aqueous solution are metered within a period of 1–2 hours at 60° C. into a solution of 228.7 g (1 mol) of 3-chloro-2-(tertbutylthio)be ehyde in 500 ml of 1-propanol. All the starting material has reacted by the time metering is complete. The solution can be used as such for the following stage. In order to isolate the product, approximately 300 ml of the solvent are distilled off, 500 ml of water are added and then approximately another 200 ml are distilled off; the product crystallises out and is isolated by filtration. Yield: 241 g (99% of the theoretical yield); m.p. 119°–121° C.

EXAMPLE 6

Preparation of 3-chloro-2-(tert-butylthio)benzalde(Compound IIIA)

98 g (1.1 mol) of tert-butylmercaptan are metered at 110° C. within a period of 4–5 hours into a suspension of 175 g (1 mol) of 2,3-dichlorobenzaldehyde and 155 g (1.12 mol) of potassium carbonate in 460 ml of N,N-dimethylformamide; the reaction mixture is then stirred for 4 hours at 120° C. The solvent is then distilled off in vacuo, the residue is washed out with 300 ml of water at 70° C., 200 ml of water are added to the organic phase at 70° C. and the batch is cooled to 30°–40° C., with stirring. During that operation, the product crystallises out and is isolated by filtration. Yield: 195 g (85% of the theoretical yield); content >96%; m.p. 52°–54° C.

What is claimed is:

1. A process for the preparation of a compound of formula I

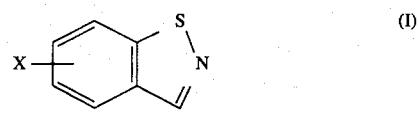

wherein
X is in any one of the 4 possible positions of the benzene ring and is halogen, in which process a compound of formula II

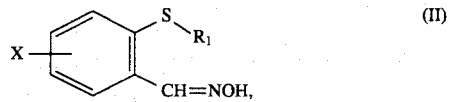

wherein
X is as defined for formula I and $R_1$ is hydrogen or an unsubstituted or substituted $C_1$–$C_{12}$hydrocarbon radical, is reacted in the presence of a catalytic amount of a strong acid and the reaction is carded out in water or a $C_1$–$C_6$alkanyl of a mixture thereof as the solvent.

2. A process according to claim 1, wherein X is in the 7-position.

3. A process according to claim 2, wherein X is chlorine.

4. A process according to claim 1, wherein in formula II $R_1$ is $C_1$–$C_6$alkyl or benzyl.

5. A process according to claim 4, wherein $R_1$ is tert-butyl.

6. A process according to claim 1, wherein 1-propanol or 2-butanol is used as the solvent.

7. A process according to claim 1, wherein a mineral acid or a sulfonic acid is used as the strong acid.

8. A process according to claim 7 wherein p-toluenesulfonic acid, methanesulfonic acid, hydroxylamine-O-sulfonic acid or sulfuric acid is used as the strong acid.

9. A process according to claim 1, wherein the strong acid is bound to a solid carrier.

10. A process according to claim 7, wherein the strong acid is used in an amount of 1–50 mol %, based on the compound of formula II.

11. A process according to claim 10, wherein the strong acid is used in an amount of 2–15 mol %, based on the compound of formula II.

12. A process according to claim 1, wherein the reaction is carried out at from 30° C. up to the reflux temperature of the solvent.

13. A process according to claim 12, wherein the reaction is carried out at the reflux temperature of the solvent and solvent is distilled off continuously.

* * * * *